US 6,555,656 B2

(12) United States Patent
Scott (10) Patent No.: US 6,555,656 B2
(45) Date of Patent: Apr. 29, 2003

(54) COVALENT MODIFICATION OF ABNORMAL PRION PROTEIN

(75) Inventor: Mark D. Scott, Clifton Park, NY (US)

(73) Assignee: Albany Medical College, Albany, NY (US)

( * ) Notice: Subject to any disclaimer, the term of this patent is extended or adjusted under 35 U.S.C. 154(b) by 69 days.

(21) Appl. No.: 09/861,306

(22) Filed: May 18, 2001

(65) Prior Publication Data

US 2002/0172977 A1 Nov. 21, 2002

(51) Int. Cl.$^7$ .................................................. C07K 1/00
(52) U.S. Cl. .................. 530/350; 424/78.08; 424/78.17; 424/78.19; 424/78.22; 424/78.25; 424/78.26; 424/78.27; 424/78.31; 424/78.32; 424/78.35; 436/503; 436/528; 544/190; 544/191; 544/192
(58) Field of Search .......................... 424/78.08, 78.17, 424/78.18, 78.19, 78.22, 78.23, 78.26, 78.27, 78.31, 78.32, 78.35; 436/503, 528; 544/190, 191, 192; 530/350

(56) References Cited

PUBLICATIONS

Farquhar et al. Prolongation of scrapie incubation period by an injection of dextran sulphate 500 within the month before or after infection. Journal of General Virology (1986) vol. 67, pp. 463–473.*
Scott et al. Chemical camouflage of antigenic determinants: stealth erythrocytes. Proceedings of the National Academy of Science (1997) vol. 94, p. 7566–7571.*

* cited by examiner

*Primary Examiner*—James Housel
*Assistant Examiner*—Ulrike Winkler
(74) *Attorney, Agent, or Firm*—Schmeiser, Olsen & Watts (57) ABSTRACT

A prion-physiological structure and associated method of formation. A provided abnormal prion has a transforming power over a normal prion to convert the abnormal prion into defective prion that mimics the abnormal prion. A linker molecule is then bonded to the abnormal prion, wherein a polymer that is covalently attached to the linker molecule facilitates formation of a polymerized abnormal prion that does not have the transforming power over the normal prion.

22 Claims, 9 Drawing Sheets

EXAMPLES OF PEG LINKER CHEMISTRY CAPABLE OF PRION COVALENT SURFACE MODIFICATION

| NAME OF POLYMERATED LINKER CHEMICAL (PLC) | TARGET OF PLC |
|---|---|
| aldehyde PEG | Reacts with Primary Amines |
| w-amino-a-carboxyl PEG | Protein Amino Groups |
| benzotriazole carbonate | Protein Amino Groups (primarily lysine) |
| carbonylimidazole PEG | Protein Amino Groups |
| cynauric chloride PEG | Protein Amino Groups (primarily lysine) |
| epoxide PEG | Amino, Hydroxyl, and Thiol groups |
| glycidyl ether (epoxide) of PEG | Amino, Hydroxyl, and Thiol groups |
| isocyanate PEG | Alcohol Groups and Amines |
| maleimide PEG | Thiol Groups |
| N-hydroxysuccinimidyl-maleimide (NHS-maleimide) | Amine and Thiol Groups |
| NHS-vinylsulfone | Amine and Thiol Groups |
| NHS-PEG2 | Amine and Thiol Groups |
| p-nitrophenylcarbonate PEG | Protein Amino Groups |
| oxycarbonylimidazole PEG | Amine Groups |
| orthopyridyl disulfide | Thiol Groups |
| phospholipid PEG | Intercalates into Lipid Membrane/Capsid Surfaces (no covalent bonding) |
| succinimidyl butanoate (SBA-PEG) | Lysine and Terminal Amines |
| succinimidyl ester of carboxymethylated PEG | Lysine and Terminal Amines |
| succinimidyl propionate (SPA-PEG) | Lysine and Terminal Amines |
| succinimidyl succinamide (SSA-PEG) | Lysine and Terminal Amines |
| succinimidyl succinate PEG (SS-PEG) | Amine Groups |
| thiol PEG | Thiol Groups |

*FIG. 5*

Examples of Human and Animal Disease Caused by Abnormal Prion Proteins

| Name | Known Genetic Mutations | Mode of Transmission |
|---|---|---|
| Human Diseases | | |
| Creutzfeld-Jacob Disease (CJD) | Proline → Leucine    Codon 102 | 85% Spontaneous (Infectious Agent?) |
| Classical Variant (Inherited?) | Aspartate → Asparagine    Codon 178 | 15% Genetic |
| New Variant (BSE Derived?) | Glutamate → Lysine    Codon 200 | 1% Iatrogenic |
| Gerstmann-Straussler-Scheinker Syndrome (GSS) | Proline → Leucine    Codon 102<br>Alanine → Valine    Codon 17 | Genetic and Spontaneous |
| Fatal Familial Insomnia (FFI) | Proline → Leucine    Codon 102<br>Aspartate → Asparagine    Codon 178 | Genetic |
| Kuru | | Cannibalism |
| Alpers Syndrome | | Genetic<br>(Possible placental transmission?) |
| Non-Human Diseases | | |
| Scrapie | | Genetic (see accompanying text);<br>Grazing (food) |
| Bovine Spongiform Encephalopathy (BSE) | | Genetic (see accompanying text);<br>Infected Animal Feed |
| Transmissible Mink Encephalopathy (TME) | | Genetic (see accompanying text) |
| Chronic Wasting Disease (CWD) of Deer | | Genetic (see accompanying text) |

NORMAL ROULEAUX FORMATION mPEG-MODIFIED RED BLOOD CELLS

COVALENT MODIFICATION OF ABNORMAL PRION PROTEIN

BACKGROUND OF THE INVENTION

1. Technical Field

The present invention relates to covalent modification of abnormal prions for protecting against transmission of prion disease.

2. Related Art

Prions are proteins that occur in the brains of all mammals studied to date. Although the normal function of a prion protein ("prion") is not well understood, recent research on mice lacking the prion protein gene (which encodes the prion protein) suggests that the prion protein protects the brain against dementia and other degenerative problems associated with old age. Such a prion is a "normal prion."

The normal prion protein (PrP) is a glycoprotein constitutively expressed on the neuronal cell surfaces of mammals. The normal prion protein can be altered, however, as a consequence of genetic mutations or induced changes in protein shape and structure (conformational changes). Indeed, such altered or "abnormal" prion proteins (also called defective prions, infective prions, distorted prions, etc.) are implicated in the pathogenesis of a number of inheritable and infectious spongiform encephalopathies in human and nonhuman animals (see FIG. 6 for both genetic and non-genetic modes of transmission). As infectious disease agents, the abnormal protein is transferred from one animal to another via multiple routes. In humans, Creutzfeldt-Jakob Disease (CJD) has been transmitted via blood transfusion (Iatrognic transmission) and a bovine derived disease (CJD-New Variant) has been though to be transmitted via the consumption of meat obtained from cattle infected with Bovine Spongiform Encephalopathy (BSE). Although some abnormal prions may be transmitted genetically, non-genetic modes of transmission are possible.

The concept of a protein as an infectious disease agent was first proposed by Prusiner in the early 1980's (Prusiner, 1982). Since the initial proposal of infectious proteins was made, the molecular/genetic basis of the some human prion diseases have been characterized as shown in FIG. 6. In addition, animals models of prion diseases have also been successfully developed.

Noteworthy aspects of diseases listed in FIG. 12 are as follows. CJD occurs when codon 129 is homozygous for valine or heterozygous for methionine and valine. Fatal Familial Insomnia (FFI) occurs when codon is 129 is homozygous for methionine. Codon 102, in relation to Gerstmann-Straussler Syndrome (GSS), produces a prion protein that accumulates in the endoplasmic reticulum. Kuru, found in the Fore tribe of New Guinea, is spread by ritual cannibalism in which mourners eat the brains of their dead relatives, a practice that has since ceased. For the non-human diseases of Scrapie, BSE, Transmissible Mink Encephalopathy (TME), and Chronic Wasting Disease (CWD) of Deer, a clear genetic predisposition is present but may not be sufficient; and some evidence suggests that an environmental agent is necessary to induce at least some genetic versions of the disease. BSE is believed to have resulted from feeding healthy cattle a processed form of sheep, wherein the sheep had died from the related disease of Scrapie.

Abnormal prions transform, via conformational changes, any normal prions they encounter into copies of themselves, as illustrated in FIG. 1. In FIG. 1, an abnormal prion 12 in a receptive host animal interacts with a normal prion 10 in the animal, resulting in a prion transformation process 14 which results in conversion of the normal prion 10 into an abnormal prion 16. The abnormal prion 12 acts as a template for the aforementioned transformation of the normal prion 10 such that the normal prion 10, when transformed to the abnormal prion 16, assumes the conformational shape of the introduced abnormal prion 12. The representation of the normal prion 10 and abnormal prion 12 in FIG. 1 is a symbolic representation of a normal prion and an abnormal prion, respectively, and does not depict or suggest the geometry of normal and abnormal prions. A normal prion includes strands of a helical shape that is called an "alpha helix" and such strands appear twisted into a spiral. An abnormal prion includes both helical strands and strands arranged in a planar shape called a "beta-sheet." The transformation process 14 of FIG. 1 converts the alpha-helix structure of the normal prion 10 into the beta-sheet structure of the abnormal prion 12.

Assuming that the transformation process 14 of FIG. 1 occurs in the brain of a host animal, the transformation process 14 continues like a chain reaction and eventually generates enough abnormal prions to cause destruction of brain neurons, resulting in an inflammatory condition in the brain that is sponge-like in appearance. Hence, abnormal prions cause brain destruction. Unfortunately, there are no known cures for prion diseases.

Since prion disease, for which there is no known cure, can be transmitted between humans, between non-human animals, and from non-human animals to humans, there are high health and economic costs relating to prion disease. Accordingly, there is a need for protecting against transmission of prion disease.

SUMMARY OF THE INVENTION

The present invention provides a method for forming a prion-physiological structure, comprising:

providing an abnormal prion that has a transforming power over a normal prion; and covalently bonding a linker molecule to the abnormal prion, wherein a polymer is covalently attached to the linker molecule to form a polymerized abnormal prion that does not have the transforming power over the normal prion.

The present invention provides a prion-physiological structure, comprising:

an abnormal prion that has a transforming power over a normal prion; and a linker molecule covalently bonded to the abnormal prion, wherein a polymer is covalently attached to the linker molecule to form a polymerized abnormal prion that does not have the transforming power over the normal prion.

The present invention provides a prion-physiological structure, comprising:

an abnormal prion that has a transforming power over a normal prion; and means for covalently bonding a linker molecule to the abnormal prion, wherein a polymer is covalently attached to the linker molecule to form a polymerized abnormal prion, and wherein the polymer has a long chain length that inactivates the transforming power.

The present invention protects against transmission of prion disease.

DETAILED DESCRIPTION OF THE INVENTION

Figure 1:
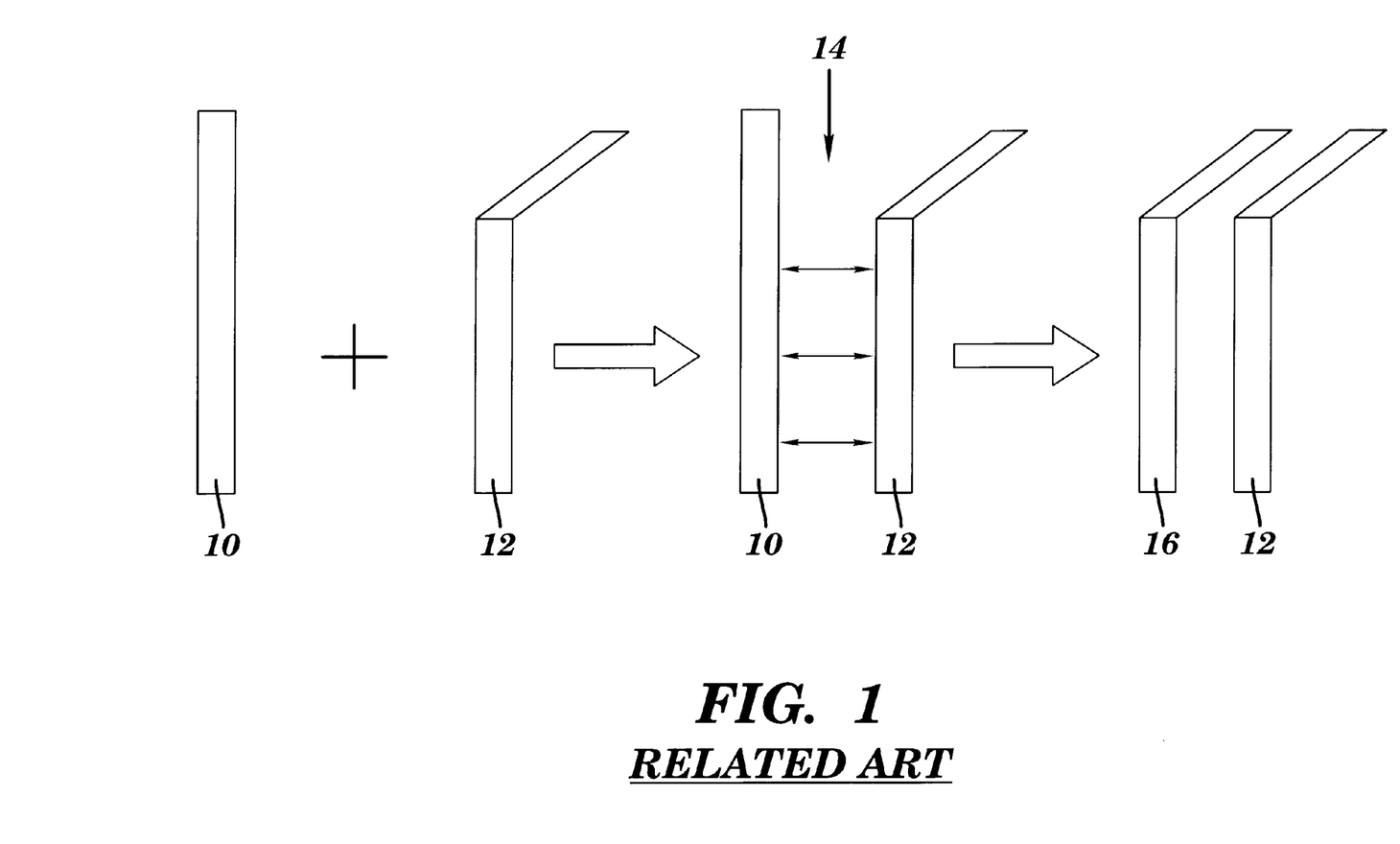
FIG. 1 depicts a transformation of a normal prion into an abnormal prion, in accordance with the related art.

An abnormal prion that is able to transform a normal prion into an abnormal prion, as described supra in conjunction with FIG. 1, is said to have a "transforming power" over the normal prion. The present invention discloses a method and structure for modifying an abnormal prion in a way that the abnormal prion so modified no longer has the transforming power over the normal prion.

Figure 2:
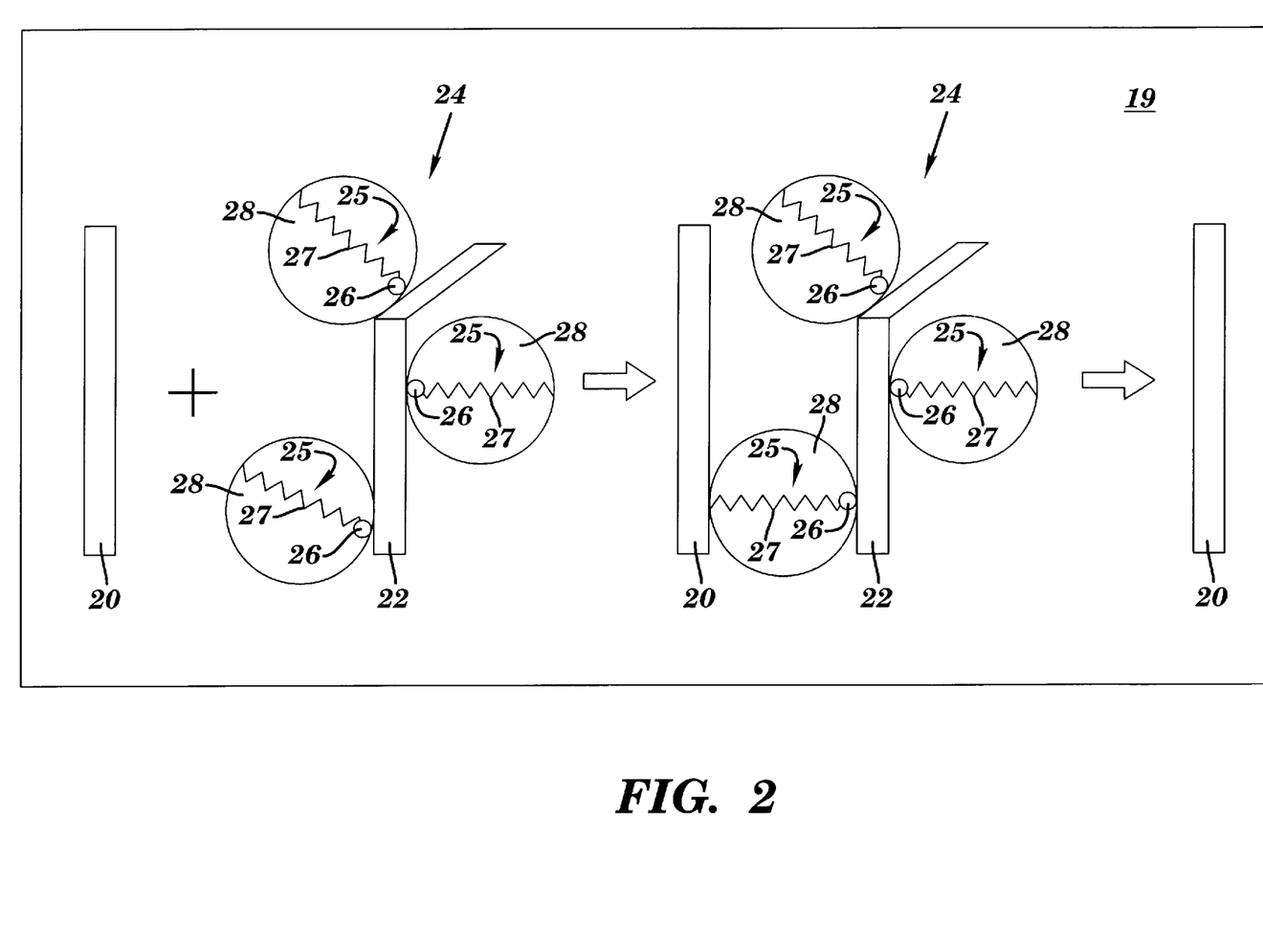
FIG. 2 depicts how polymerization of an abnormal prion prevents transformation of a normal prion into an abnormal prion, in accordance with the embodiments of the present invention.

FIG. 2 illustrates how the present invention prevents transformation of a normal prion into an abnormal prion (which removes the transforming power from the abnormal prion), in accordance with the embodiments of the present invention. In FIG. 2, a normal prion protein 20 is proximate an abnormal prion protein 22 that has been covalently bonded to a polymerated linker chemical 25 to form a polymerized abnormal prion 24. The polymerized abnormal prion 24 comprises the abnormal prion protein 22 covalently bonded to the polymerated linker chemical 25. The polymerated linker chemical 25 includes a linker molecule 26 with a covalently attached polymer 27. The polymerated linker chemical 25 is said to represent an activated form of the polymer 27. For example, if the polymer is methylpolyethylene glycol (mPEG), then "activated mPEG" is exemplified by having mPEG covalently bonded to the linker molecule of cyanuric chloride. As another example, if the polymer is polyethylene glycol (PEG), then then "activated PEG" is exemplified by having PEG covalently bonded to the linker molecule of cyanuric chloride. The linker molecule 26 is covalently bonded to a protein or carbohydrate of the abnormal prion 22. The covalent linking of the linker molecule 26 to a protein may include a covalent linking of the linker molecule 26 to an amino acid in the protein or to a sulfhydryl group in the protein. The polymer 27 has a "long chain length;" i.e., a chain length that is of sufficient magnitude to fill the space around itself to create the blocker envelope 28. The blocker envelope 28 constitutes a barrier that prevents the abnormal prion 22 from interacting with the normal prion 20. In addition, the polymer 27 within the blocker envelope 28 inhibits, by steric hindrance, interaction between the abnormal prion 22 and the normal prion 20. Additionally, the polymer 27 may be highly hydrophillic so as to create a hydration zone around itself to alternatively create the blocker envelope 28. Inasmuch as the abnormal prion 22 and the normal prion 20 would interact via a charge—charge coupling mechanism, the hydration zone encompassed by the blocker envelope 28 effectively camouflages molecular charge sites at the abnormal prion 22 and thus prevents the electrical interactions that would cause the normal prion 20 to be transformed into an abnormal prion. Thus in FIG. 2, the normal prion 20 is not transformed into an abnormal prion, because the polymerized abnormal prion 24 does not have the transforming power over the normal prion 20.

The blocker envelope 28 may be generated by the polymer 27 by any suitable method for bonding the polymerated linker chemical 25 to abnormal prion 22, such as, inter alia, spraying the polymerated linker chemical 25 onto the abnormal prion 22, immersing the abnormal prion 22 into a liquid medium that includes the polymerated linker chemical 25, reacting the polymerated linker chemical 25 with the abnormal prion 22 with further processing to create a pill that includes the polymerated linker chemical 25 enveloped around the abnormal prion 22, etc.

In FIG. 2, the interaction (or lack thereof) between the normal prion 20 and the abnormal prion 22 takes place in an environment 19. As an example, the environment 19 may comprise proteinaceous matter such as, inter alia, blood albumin intended for subsequent introduction into a human or non-human animal. Unfortunately, present technology is unable to test for abnormal prions in blood albumin. Thus, by removing the transforming power of any abnormal prions that may be present in the blood albumin, the present invention enables said subsequent introduction of the blood albumen into a human or non-human animal to be accomplished with little or no risk of infecting the animal with prion disease. As another example, the environment 19 may comprise the brain of the human or non-human animal into which the polymerized abnormal prion 24 has been introduced.

Figure 3:
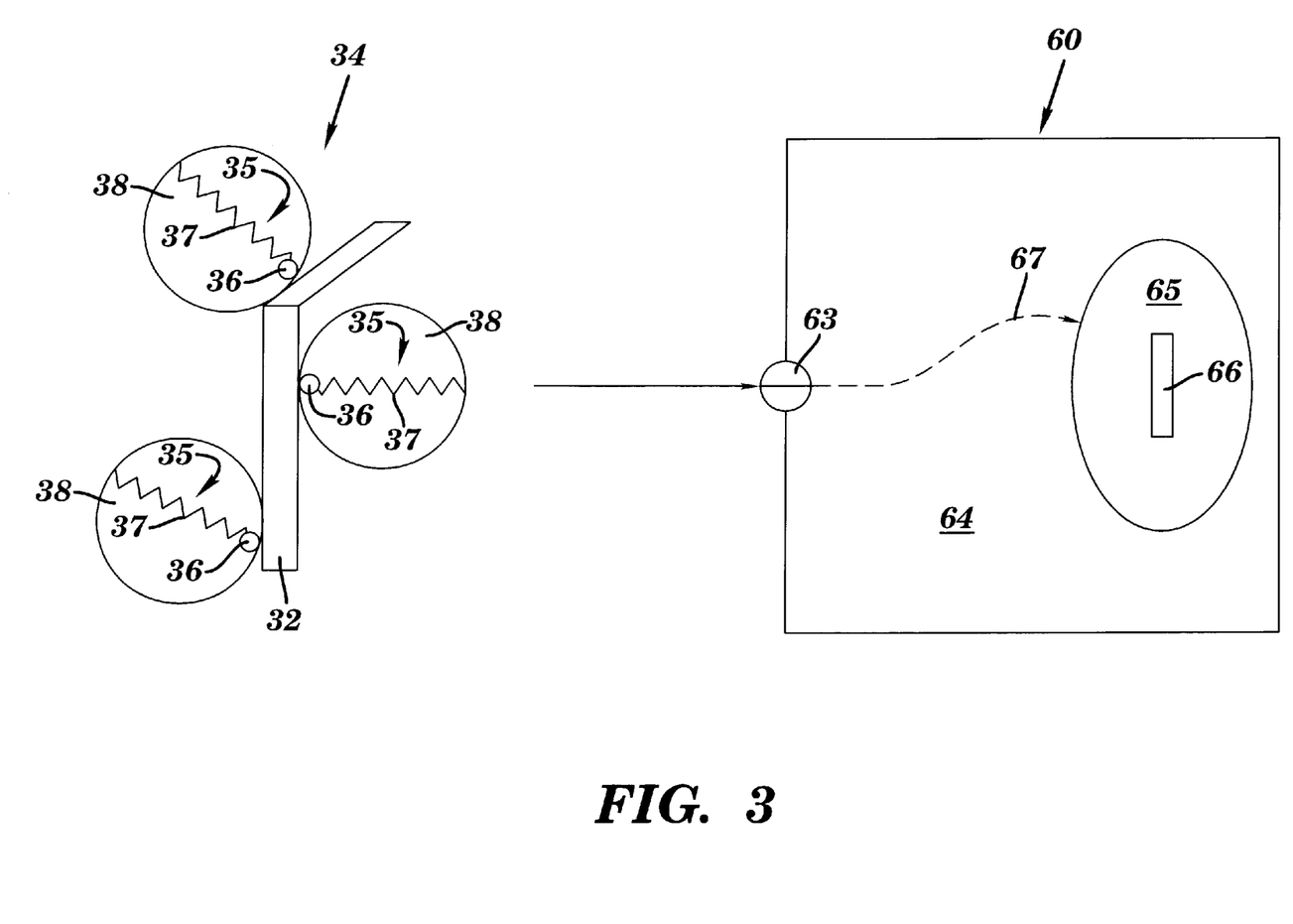
FIG. 3 depicts introduction of polymerized abnormal prion into an animal, in accordance with embodiments of the present invention.

FIG. 3 depicts introduction of polymerized abnormal prion 34 into an animal 60, in accordance with the embodiments of the present invention. The polymerized abnormal prion 34 includes a polymerated blocker chemical 35 covalently bonded to an abnormal prion 32. The polymerated blocker chemical 35 comprises a polymer 37 covalently attached to a linker molecule 36. The polymer 37 includes a blocker envelope 38.

The animal 60 may be a human animal (e.g., a human being or a fetus) or a veterinary animal. A veterinary animal is a non-human animal of any kind such as, inter alia, a domestic animal (e.g., dog, cat, etc.), a farm animal (cow, sheep, pig, etc.), a wild animal (e.g., a deer, fox, etc.), a laboratory animal (e.g., mouse, rat, monkey, etc.), an aquatic animal (e.g., a fish, turtle, etc.), etc. The animal 60 has an interior 64 which includes a brain 65 that contains a normal prion 66.

The polymerized abnormal prion 34 enters the animal 60 through an entry 63. The entry 63 denotes any entry into the animal 60 into which, or through which, the polymerized abnormal prion 34 may enter the animal 60. The polymerized abnormal prion 34 may enter the animal 60 through the entry 63 by any method or mechanism that is known to one of ordinary skill in the art for introducing a prion into an animal (or any possible method or mechanism if said entry is unintentional) such that the polymerized abnormal prion 34 that enters the animal 60 is subsequently transported into the brain 65 of the animal 60 through any physiological pathway (e.g., a vascular pathway) 67. Entry of the polymerized abnormal prion 34 into the animal 60 through the entry 63 is illustrated by the following examples. As a first example, the entry 63 may be a mouth into which the polymerized abnormal prion 34 enters in pill, liquid, or spray form, or by food consumption (e.g., beef bouillon cubes). As a second example, the entry 63 may be a nose into which the polymerized abnormal prion 34 enters by a nasal spray. As a third example, the entry 63 may be a blood vessel into which the polymerized abnormal prion 34 enters by transfusion or injection. As a fourth example, the entry 63 may be a muscle into which the polymerized abnormal prion 34 enters by needle injection. As a fifth example, the entry 63 may be a vagina (if the animal 60 is female) into which the polymerized abnormal prion 34 enters via use of a syringe (e.g., use of prion contaminated cattle semen).

There are various circumstances under which the polymerized abnormal prion 34 may enter into the animal 60, including, inter alia, the following circumstances. A first circumstance includes introducing a blood product (e.g., blood albumin from blood plasma) into the animal 60, where it has not (or cannot) be determined whether the blood product contains any prions. A second circumstance includes introducing a food product into the animal, where the food product has been previously treated with a polymerated linker chemical to covalently bond with any abnormal prions contained within the food product. A third circumstance includes introducing the polymerized abnormal prion 34 into a non-human animal for purposes of research relating to interactions between the polymerized abnormal prion 34 and the normal prion 66 in the brain 65.

FIGS. 2 and 3 show "prion-physiological structures." A prion-physiological structure is defined herein as an organic structure that includes a prion, together with any animal that comprises the prion and with any chemical that is covalently bonded to the prion.

Figure 4:
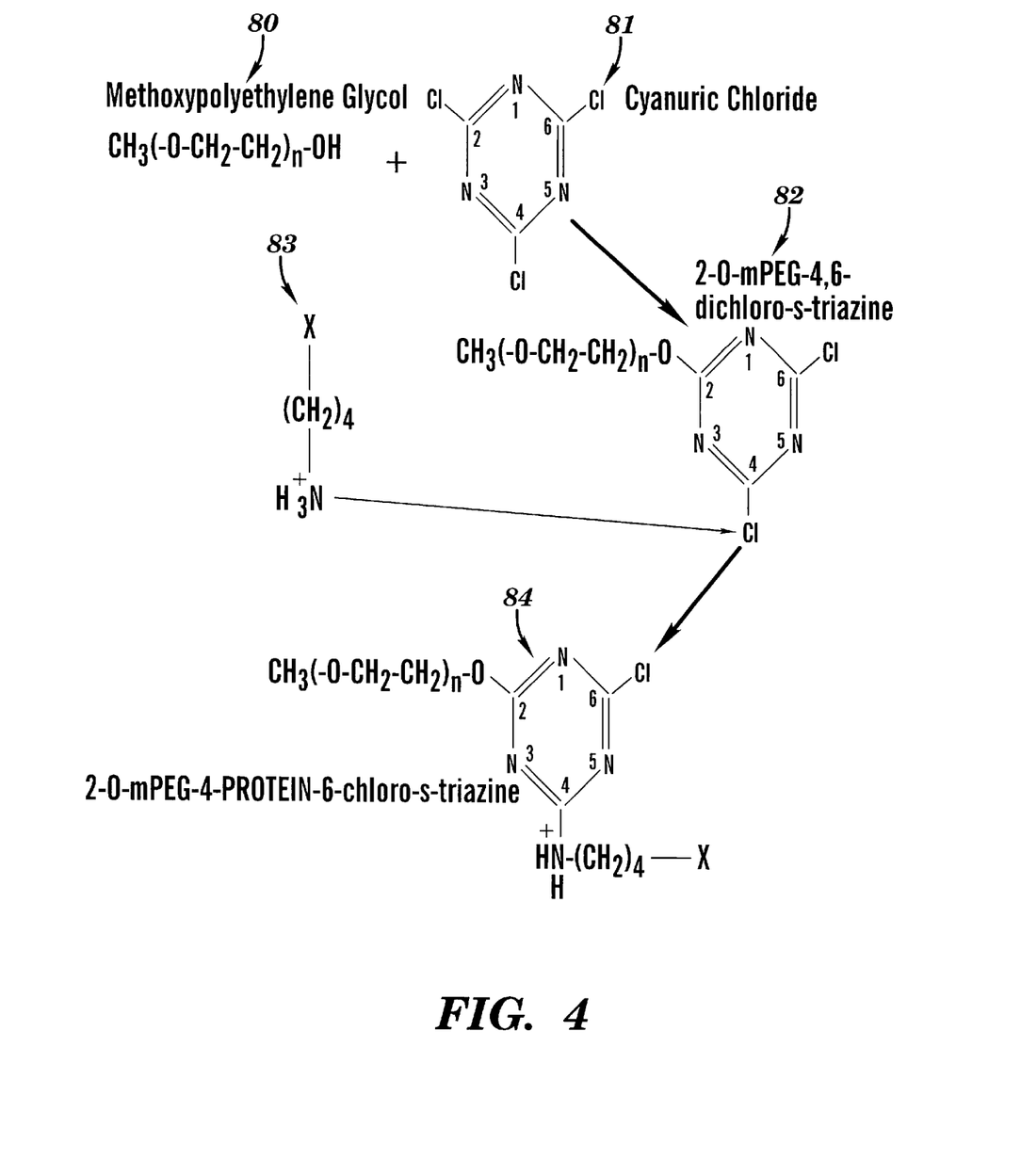
FIG. 4 depicts an exemplary chemistry of coupling a polymerated linker chemical to protein in an abnormal prion, in accordance with embodiments of the present invention.

FIG. 4 illustrates an exemplary chemistry of coupling the polymerated linker chemical (as depicted in FIG. 2 or FIG. 3) to a prion, in accordance with embodiments of the present invention. In FIG. 4, two chemical reactions are illustrated. In the first chemical reaction shown in FIG. 4, a polymer 80 reacts with a linker molecule 81 to form a polymeric linker chemical (PLC) 82 in which the polymer 80 is covalently bonded to the linker molecule 81. Specifically in FIG. 4, the polymer 80 is methoxypolyethylene glycol (mPEG) having the chemical structure of $CH_3(-O-CH_2-CH_2)_n-OH$ wherein $n \geq 2$. The linker molecule 81 is an alkyl halide (namely, cyanuric acid) and the resultant PLC 82 is 2-O-mPEG-4,6-dichloro-s-triazine. In the first chemical reaction, the hydroxyl group ($OH^{31}$) is a nucleophile that reacts generally with an alkyl halide (specifically, cyanuric chloride), resulting in displacement and release of the chlorine ion ($CL^-$) in position 2 of the cyanuric chloride triazine ring as well as release of the hydrogen ion ($H^-$) from the hydroxy group of the mPEG. The first chemical reaction may be implemented in any manner known to one of ordinary skill in the art such as in, inter alia, anhydrous benzene at a temperature of about 25° C. Formation of the PLC 82 of 2-O-mPEG-4,6-dichloro-s-triazine is well-known in the art and may be obtained commercially.

In the second chemical reaction shown in FIG. 4, a protein 83 reacts with the PLC 82 to form a protein-polymer complex 84. Specifically in FIG. 4, the protein 83 includes lysine, wherein $H_3N^+-(CH_2)_4$ is a portion of the lysine that reacts with the PLC 82, and wherein X represents a remaining portion of the protein 83 including a remaining portion of the lysine. The remaining portion of the lysine has a carbon atom covalently bonded to H, $H_3N^+$, and a carboxyl group. As shown in FIG. 4, a hydrolysis of the chlorine in position 4 of the cyanuric chloride triazine ring has replaced said chlorine in position 4 with the $H_3N^+-(CH_2)_4$ portion of the lysine of the protein 83, to form the protein-polymer complex 84. Specifically in FIG. 4, the protein-polymer complex 84 is 2-O-mPEG-4-Y-6-chloro-s-triazine, wherein Y is the protein $H_3N^+-(CH_2)_4-X$. More generally, FIG. 4 shows generation of a PEG-conjugated protein with attachment of an activated PEG (e.g., the PLC 82) to an e-amino group (e.g., the lysine or another amino acid such as arginine). The second chemical reaction may be implemented in an alkaline phosphate buffer (e.g., 50 mM of $K_2HPO_4$ and 105 mM of NaCl, wherein mM denotes millimoles). The second reaction can be efficiently accomplished in a wide range of media including, inter alia, saline, phosphate buffered saline, blood plasma, blood serum, albumin containing buffers, Hanks Balanced Salt Solution (HBSS), N-[2-hydroxyethyl]piperazine-N'-2-ethanesulfonic acid ("HEPES"), Roswell Park Memorial Institute 1640 ("RPMI 1640"), etc.

Time and temperature for performing the second reaction are very flexible. For example, a reaction between mPEG and an amino acid of a prion may be accomplished in 4 minutes or longer at 4° C. if the pH is about 9. If the pH is lower (e.g., about 8), the reaction may proceed at room temperature for a longer period (e.g., 60 minutes or longer) so that the virus is stressed by temperature and not stressed by harsh alkaline conditions. As to pH, it is useful to have a pH of about 8 when reacting mPEG with lysine. When reacting mPEG with a prion, weakly acidic to alkaline conditions should be used with a representative pH range of about 6.0 to about 9.0.

Effective doses of the PLC in the second reaction depend on several variables, including: linker chemistry, the polymer being used, surface area of prion surfaces being modified, etc.

It should be noted that the chlorine in position 6 of the cyanuric chloride triazine ring is quite unreactive and thus unavailable to react with either an amino acid or with a second polymerated linker chemical.

Figure 5:
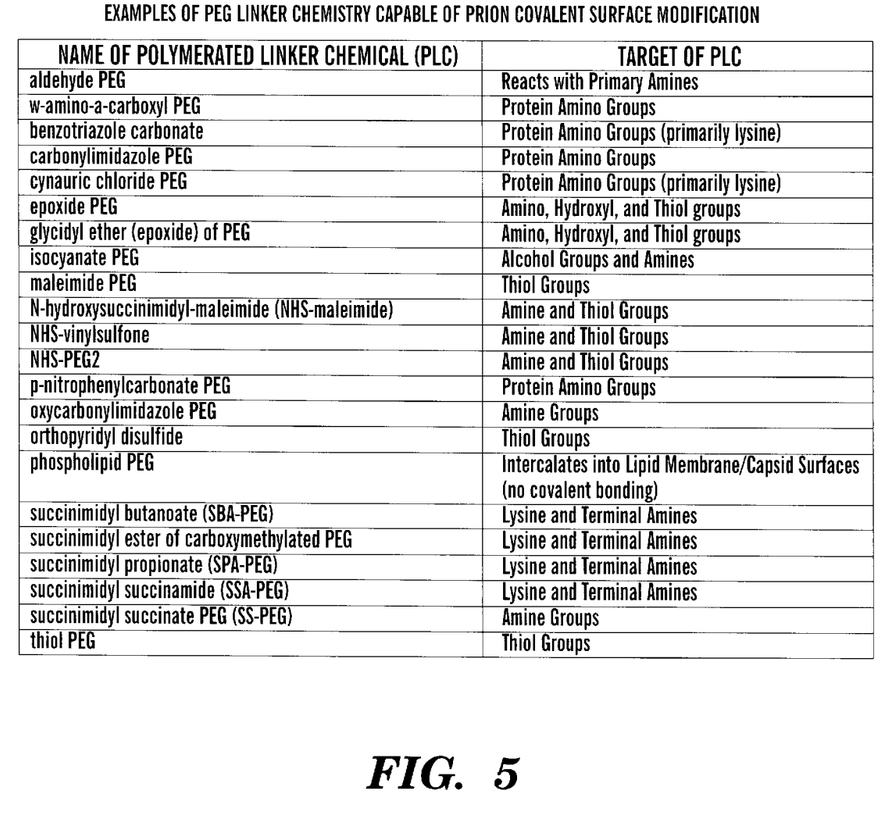
FIG. 5 lists exemplary polymeric linker compounds and associated protein or carbohydrate targets that can be reacted with the exemplary polymeric linker compounds, for use in conjunction with FIGS. 2 and 3, and in accordance with embodiments of the present invention.

FIG. 4 illustrates a mechanism of the covalent attachment of the polymerated linker chemical of cyanuric chloride coupled methoxypolyethylene glycol (mPEG) with protein of a prion, and potentially with carbohydrate of a prion. All known prions include protein structure that can be similarly modified via the present invention with only slight variations in pH, temperature and time. Indeed, the pH, time and temperature conditions at which the modification reaction can be done at are very malleable, thus making this invention applicable to a wide variety of prion types. Other polymers may be utilized instead of mPEG, such as, inter alia, polyethylene glycol, ethoxypolyethylene glycol, dextran, FICOLL®, and arabinogalactan. FICOLL® is trademark representing a polymer of sucrose formed by copolymerization of sucrose with epichlorohydrin, said sucrose polymer being neutral, highly branched, hydrophilic and dissolving readily in an aqueous solution (hereinafter "sucrose polymer"). Other linker molecules may be utilized instead of cyanuric chloride, such as, inter alia, imidazolyl formate, succinimidyl succinate, succinimidyl glutarate, N-hydroxysuccinimide, 4-Nitrophenol, 2,4,5-trichlorophenol, and a chloroformate. FIG. 5 lists exemplary polymeric linker compounds (PLCs) that may be used with the present invention and associated targets that can be reacted with the PLCs. Most of the listed targets in FIG. 5 are proteins. The thiol groups in FIG. 5 include sulfhydryl groups which are protein components. Any of the PLCs that react with the hydroxyl group can be reacted with a carbohydrate. Note that the PLC of phospholipid PEG interacts with a lipid by intercalation rather than by covalent bonding.

As discussed supra, the present invention is based on interactions between abnormal prions and normal prions. Such interactions may be understood in terms of protein—protein and charge—charge coupling models, which are explained and confirmed as follows.

Animal models have conclusively demonstrated that prion disease can be transmitted via food consumption or direct injection. The basic disease process is dependent upon the interaction of the abnormal PrP protein with the normal PrP protein (Scott et al. 1989; Scott et al. 1993). This protein—protein interaction results in a conformational change in the normal PrP protein. Zahn et al. (2000) demonstrated that in sheep the conformational transition to the scrapie form of PrP, which causes prion disease, is due to direct inter-molecular interactions between the abnormal and normal PrP proteins. The effective transmission of prion diseases depends on the abnormal prion being similar enough to the host's normal prion protein to be able to 'lock in' to its structure and convert it. The disease pathogenesis does not require any genetic alteration in the infected animal.

As is well established in the scientific literature, all proteins have an 'optimal' folding pattern that is mediated by intra-protein and inter-protein charge—charge interactions and amino acid hydrophobicity and hydrophilicity (Mirny et al., 2001). The 'optimal' shape is a stable low energy state that is determined via the above hydrophobicity, hydrophilicity, and charge—charge interactions. The more hydrophobic (oily) an amino acid is, the less stable it is when surrounded by water thus favoring the self-aggregation of hydrophobic residues and the exclusion of water while the hydrophilic residues fold so as to be in contact with water. This folding in turn is affected by the electrical charge and the physical size of amino acids. All of these factors balance against each other until the protein twists into a stable, low energy state where the hydrophobic amino acids stabilize each other, and opposite intra-chain and/or inter-chain charges are close together (charge—charge interactions). It is further established that proteins undergo significant conformational changes within cells both in vivo and in vitro. These changes include initial protein folding and subsequent unfolding, refolding, and transitional folding states that are induced by intra-protein and inter-protein charge—charge interactions and substrate binding. These charge—charge interactions are in turn influenced by the intra- and extra-cellular environment including pH, energy state, oxidant injury, and phosphorylation status. The optimal protein structure can in turn be influenced by other proteins. For example, chaperone proteins are a class of proteins that traffic proteins within the cell, protect the protein against degradation, and assist in proper protein folding and refolding following biologic insult. However, as with intra-chain folding, the protein—protein (e.g., chaperone) mediated folding is also governed by charge—charge interaction and hyrophilic/hydrophobic interactions (Panse et al., 2000). Protein conformation can also be altered by substrate binding, as well as protein phosphorylation, both of which altering the surface charge characteristics of a protein. An example of a substrate induced conformational change in a protein is seen in myosin which undergoes a significant structural change following binding of adenosine triphosphate (ATP) binding and ATP hydrolysis (Rayment, 1993).

While at least two distinct mechanisms have been proposed to account for an ability of the abnormal PrP protein to induce changes in the normal protein, both mechanisms employ the same mechanisms of protein folding used to explain normal protein folding (Horiuchi et al., 1999; Prusiner, 1991; Jarrett and Lansbury, 1993; Cohen et al., 1994). Specifically, charge—charge, hydrophilic/hydrophobic, and protein—protein changes in conformation are involved in PrP disease pathogenesis. To accomplish this conformational change by the abnormal PrP protein, the coaggregation of the abnormal and normal PrP protein is a crucial event. This aggregation event allows for the close proximity of the abnormal and normal PrP protein and further enhances the relative concentration of the two proteins. Indeed, the relative concentration of the two proteins is important and is referred to as the nucleation (aggregation) event. Studies suggest that the initial nucleation (aggregation) event requires a critical mass (volume) of abnormal and normal PrP protein (Horiuchi et al., 2000; Prusiner, 1991). In this conformational change event, the abnormal PrP protein acts as a template for the refolding of the normal protein.

Figure 6:
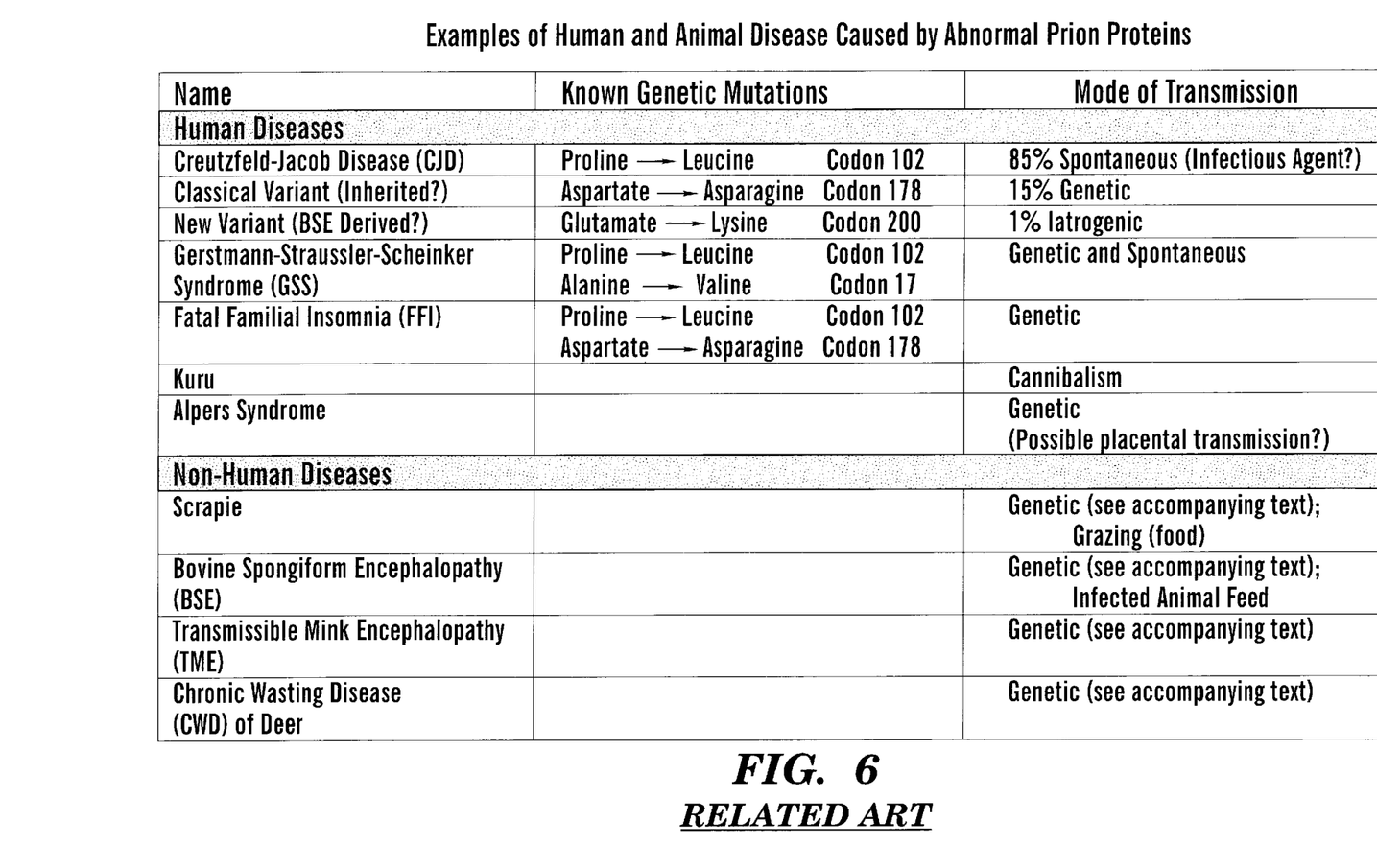
FIG. 6 lists examples of human and animal diseases caused by abnormal prion proteins, in accordance with the related art.

Hence, as described by the existing prion literature, a critical event in prion disease is the direct physical association of the abnormal PrP protein with the normal cellular homolog in this nucleation (aggregation) event (Horiuchi et al., 2000). This is shown diagrammatically in FIG. 1. Hence, prevention of this interaction could prove beneficial in preventing or delaying the onset of prion-mediated disease in human and nonhuman animals. The interaction of the abnormal prion protein can be prevented by agents that give rise to improved solubility (i.e., prevents aggregation of the protein) or prevents the physical interaction of the abnormal and normal PrP proteins. As described in this invention, the covalent modification of the abnormal prion with polyethylene glycol (or its derivatives), dextran, or arabinogalactan, or any combination thereof as depicted in FIG. 5 and discussed supra, can prevent the conformation change of the normal PrP protein. Said prevention of conformational change disables or removes the "transforming power" of the abnormal prion as discussed supra in conjunction with FIG. 2. For example, derivatization of the abnormal protein with methoxypoplyethylene glycol does the following: (1) improves solubility of the abnormal protein which diminishes the aggregation and critical nucleation event, as described by Horiuchi et al. (2000); and (2) prevents protein—protein interaction necessary for conformational conversion, as described by Prusiner (1991), Horiuchi et al. (2000), and others, by blocking charge—charge interactions as well as sterically hindering the stable interaction of the abnormal and normal PrP proteins. Furthermore, as shown in FIG. 6, one abnormal human protein associated with Creutzfeldt-Jakob Disease occurs as a consequence of a single amino acid substitution of glutamate → lysine at codon 200 (cited in some literature as codon 199) of a mutant human PrP gene/protein. The presence of this lysine group serves as a potential target for a number of activated PEG agents as listed in FIG. 5 thus serving as an additional manner of preventing protein—protein interaction. The sequence of normal and abnormal PrP proteins has been elucidated and is highly amenable to covalent derivatization with activated PEG species due to the presence of multiple lysine residues as well as other targets for PEG-derivatization. See Stahl et al. (1993).

Figure 8:
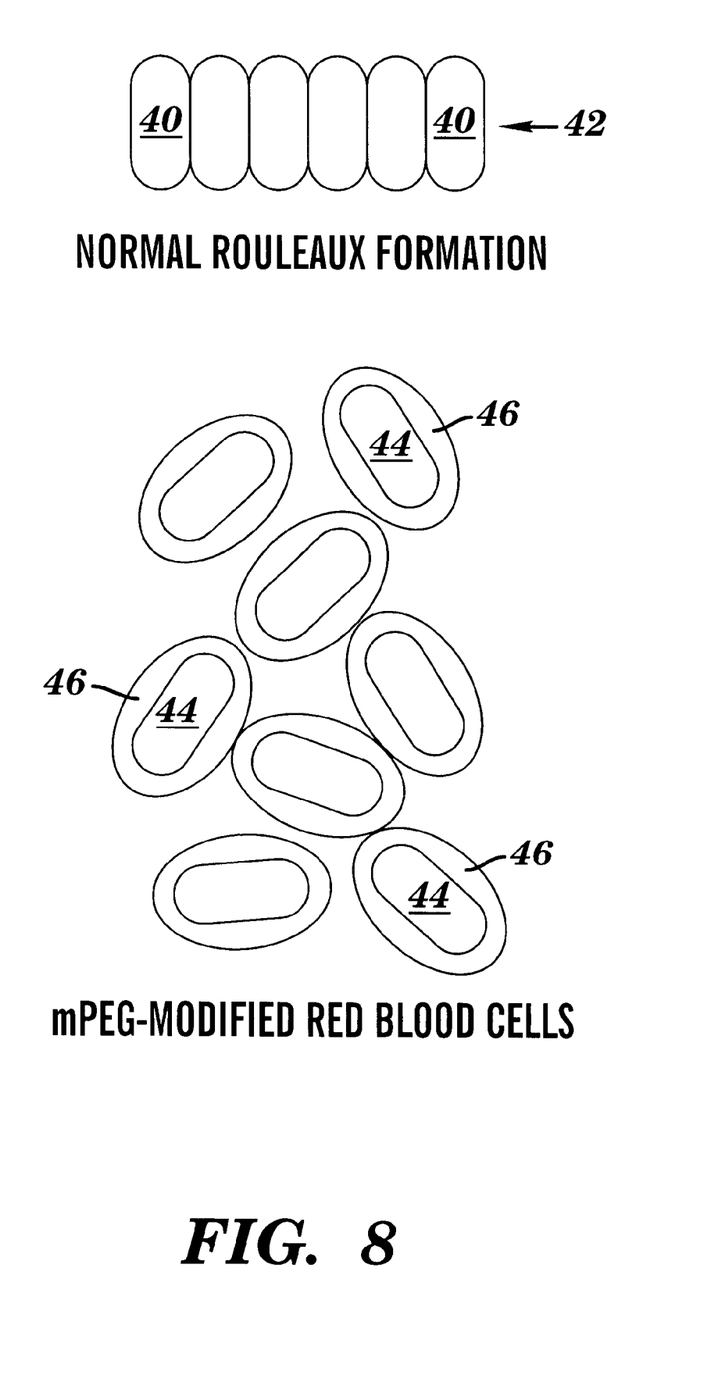
FIG. 8 depicts loss of red blood cell Rouleaux Formation, resulting from pegylation of the red blood cells.
Figure 9:
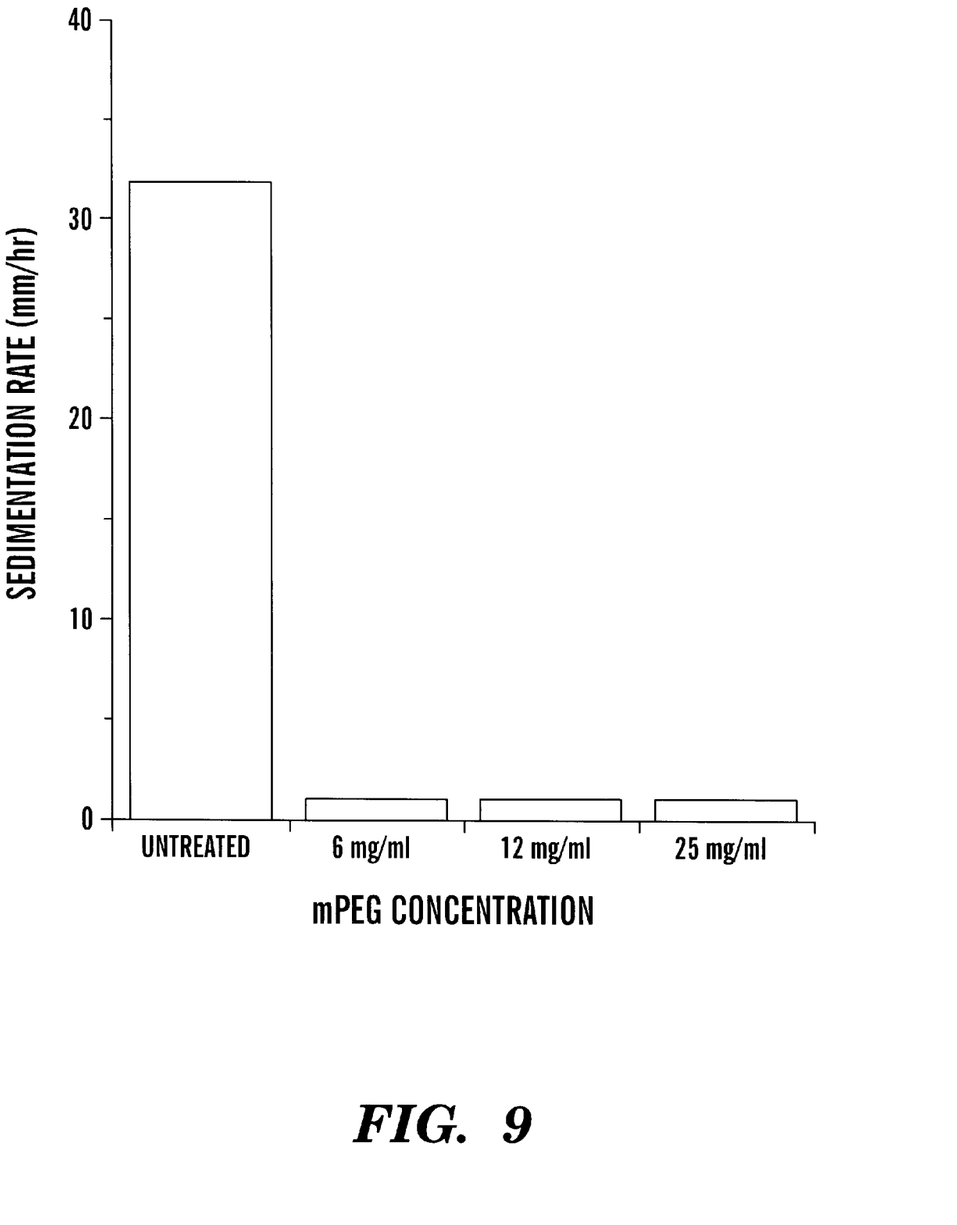
FIG. 9 depicts non-sedimentation of red blood cells, resulting from pegylation of the red blood cells.

Biophysical, biochemical, and physiologic evidence that clearly provide foundational support this invention are summarized as follows. First as previously discussed, in the absence of a normal PrP protein (e.g., PrP knockout mice) the introduction of abnormal PrP does not induce disease (Sakaguchiet al, 1996; Brander et al, 1996). Hence, interaction of the abnormal and normal PrP proteins is essential for disease pathogenesis. Second, as discussed supra, conformational changes in proteins are associated with proteinaceous folding patterns, and said folding patterns result from intra-protein and inter-protein interactions which are generally governed by charge—charge coupling and nucleation (aggregation) processes. Third, studies of pegylated proteins and cells teach that pegylation camouflages the inherent charge of proteins, thus preventing charge—charge associations. This is evidenced by the loss of movement in an electrical filed, which demonstrates the apparent loss of surface charge. See FIG. 7 (Scott and Bradley et al., 2000) discussed infra. Fourth, our studies demonstrate that pegylated proteins and cells demonstrated reduced abilities to aggregate (i.e., undergo nucleation events). See FIGS. 8 and 9 (Scott and Mahaney et al., 2000) discussed infra. Fifth, pegylated proteins and cells demonstrate enhanced solubility as evidenced by the improved solubility (i.e., inability to sediment) of red blood cells ("RBC") (FIG. 9; Scott and Mahaney et al., 2000). These events of FIGS. 8 and 9 are evidenced by the loss of Rouleaux formation (the stacking/aggregation of RBC) and the subsequent loss of red blood cell sedimentation (settling). Similarly, studies of PEG-modified purified proteins and lipid particles also clearly demonstrated that their half-life within the circulation/tissue is significantly improved (see Herschfield, 1987; Beckman, 1988; Abuchowski, 1984; Zalipsky; 1994; Maruyama, 1992). Finally, receptor-ligand (a more complex protein—protein interaction) is prevented by all of the above events (Scott et al., 1998; Scott and Bradley et al., 2000). As demonstrated by the above points, pegylation of proteins effectively prevents/diminishes the nucleation (aggregation) process necessary for prion disease pathogenesis. The preceding biophysical, biochemical, and physiologic evidence provides foundational support for the method and structure of the present invention as depicted in FIG. 2.

Figure 7:
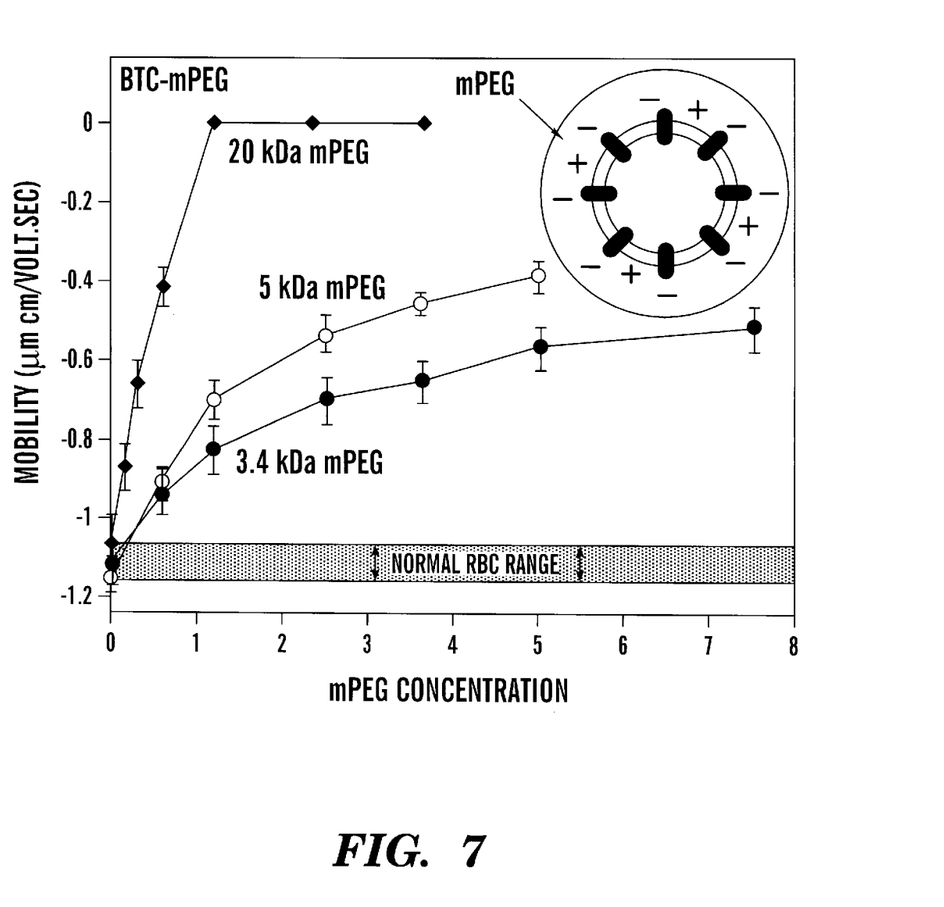
FIG. 7 depicts loss of mobility of red blood cells in an electric field, resulting from pegylation of the red blood cells.

In FIG. 7 from Scott and Bradley et al. (2000), covalent attachment of mPEG to the red blood cells (RBC) significantly reduces the mobility of the cell in an applied electrical field. Loss of mobility is mediated by both the camouflage of the inherent surface charge of the RBC and the increased drag placed on the cell by the covalently attached mPEG polymers. Electrophoretic mobility measurements of control and pegylated RBC were made on a Rank Mark I electrophoresis apparatus equipped with a horizontal microscope having a water immersion lens. Ten different RBC were chosen randomly and were manually timed to determine their velocity in the field. The electrophoretic mobility was determined as: mobility=velocity of the particle ($\mu$m/sec)/electric field strength (E) in volt/cm; where E=(voltage/distance between the electrodes). RBC's were covalently modified with benzotriazole carbonate of mPEG ("BTC-mPEG") containing polymers of increasing molecular weight (3.4, 5, and 20 kDa). The RBC were covalently modified in isotonic saline and washed 3-time in saline prior to electrophoretic mobility determinations. The mPEG concentration is shown in millimoles of mPEG per liter (mMol/L) of the isotonic saline medium. At 20 kDa mPEG, a null electrophoretic mobility was achieved at an mPEG concentration of about 1.2 mMol/L and higher, resulting in a total camouflaging of surface charge. At 5 kDa mPEG and 3.4 kDa mPEG, a partial camouflaging of surface charge was achieved at the highest mPEG concentrations, corresponding to a reduction of about a factor of 3.0 and 2.0, respectively in electrophoretic mobility. Thus, the camouflaging of surface charge becomes increasingly effective with increasing polymeric molecular weight and also with increasing mPEG concentration (until zero mobility is achieved).

In FIG. 8, pegylation of cells and proteins results in the camouflage of protein associated charge. As a consequence of the obfuscation of protein charge, protein-mediated aggregation is prevented. This is evidenced by the loss of red blood cell Rouleaux Formation (stacking) which is charge-mediated. As shown at top, normal red blood cells 40 form stacking structures 42 due to membrane surface (protein—protein) interactions. However, covalent attachment of mPEG 46 to red blood cells 46, or its derivatives, camouflages the inherent charge of the membrane surface proteins, which prevents the required protein—protein interactions necessary for cell stacking and Rouleaux formation.

In FIG. 9, pegylation of cells and proteins results in the camouflage of protein associated charge. This is evidenced by the loss of movement of particles in an electrical field as shown in FIG. 7 and discussed supra. Because of the obfuscation of protein charge, protein-mediated aggregation is prevented. This is evidenced by the loss of red blood cell Rouleaux Formation (stacking) which is charge-mediated as shown in FIG. 8 and discussed supra. As shown in FIG. 9, normal untreated red blood cells serve as a control and have a sedimentation rate of about 32 mm/hr. In contrast, consequent to the loss of microaggregation, mPEG-modified red blood cells have a measured sedimentation rate of only about 1 mm/hr, which is within the noise level of the measurement instrumentation. Thus, the mPEG-modified red blood cells no longer sediment and therefore remain soluble in solution (i.e., have improved solubility).

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method for forming a prion-physiological structure, comprising:
   providing an abnormal prion that has a transforming power over a normal prion; and
   covalently bonding a linker molecule to the abnormal prion, wherein a polymer is covalently attached to the linker molecule to form a polymerized abnormal prion that does not have the transforming power over the normal prion.

2. The method of claim 1, wherein the polymer is selected from the group consisting of polyethylene glycol, methoxypolyethylene glycol, ethoxypolyethylene glycol, dextran, sucrose polymer, and arabinogalactan.

3. The method of claim 1, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

4. The method of claim 1, wherein the abnormal prion has human significance.

5. The method of claim 1, wherein the abnormal prion has veterinary significance.

6. The method of claim 1, wherein covalently bonding the linker molecule to the abnormal prion includes covalently bonding the linker molecule to an amino acid at the abnormal prion.

7. The method of claim 1, wherein covalently bonding the linker molecule to the abnormal prion includes covalently bonding the linker molecule to a lysine group at the abnormal prion.

8. The method of claim 1, wherein covalently bonding the linker molecule to the abnormal prion includes covalently bonding the linker molecule to a carbohydrate at the abnormal prion.

9. The method of claim 1, wherein covalently bonding the linker molecule to the abnormal prion includes covalently bonding the linker molecule to a sulfhydryl group at the abnormal prion.

10. A method for forming a prion-physiological structure, comprising:

providing an abnormal prion that has a transforming power over a normal prion; and covalently bonding a linker molecule to the abnormal prion, wherein a polymer is covalently attached to the linker molecule to form a polymerized abnormal prion, and wherein the polymer has a long chain length that inactivates the transforming power.

11. A method for forming a prion-physiological structure, comprising:

providing an abnormal prion that has a transforming power over a normal prion; and covalently bonding a linker molecule to the abnormal prion, wherein a polymer is covalently attached to the linker molecule to form a polymerized abnormal prion, and wherein a camouflaging by the polymer of a charge site at the abnormal prion inactivates the transforming power.

12. A prion-physiological structure, comprising:

an abnormal prion that has a transforming power over a normal prion; and a linker molecule covalently bonded to the abnormal prion, wherein a polymer is covalently attached to the linker molecule to form a polymerized abnormal prion that does not have the transforming power over the normal prion.

13. The prion-physiological structure of claim 12, wherein the polymer is selected from the group consisting of polyethylene glycol, methoxypolyethylene glycol, ethoxypolyethylene glycol, dextran, sucrose polymer, and arabinogalactan.

14. The prion-physiological structure of claim 12, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

15. The prion-physiological structure of claim 12, wherein the abnormal prion has human significance.

16. The prion-physiological structure of claim 12, wherein the abnormal prion has veterinary significance.

17. The prion-physiological structure of claim 12, wherein covalently bonding the linker molecule to the abnormal prion includes covalently bonding the linker molecule to an amino acid at the abnormal prion.

18. The prion-physiological structure of claim 12, wherein covalently bonding the linker molecule to the abnormal prion includes covalently bonding the linker molecule to a lysine group at the abnormal prion.

19. The prion-physiological structure of claim 12, wherein covalently bonding the linker molecule to the abnormal prion includes covalently bonding the linker molecule to a carbohydrate at the abnormal prion.

20. The prion-physiological structure of claim 12, wherein covalently bonding the linker molecule to the abnormal prion includes covalently bonding the linker molecule to a sulfhydryl group at the abnormal prion.

21. A prion-physiological structure, comprising:

an abnormal prion that has a transforming power over a normal prion; and a linker molecule covalently bonded to the abnormal prion, wherein a polymer is covalently attached to the linker molecule to form a polymerized abnormal prion, and wherein the polymer has a long chain length that inactivates the transforming power.

22. A prion-physiological structure, comprising:

an abnormal prion that has a transforming power over a normal prion; and a linker molecule covalently bonded to the abnormal prion, wherein a polymer is covalently attached to the linker molecule to form a polymerized abnormal prion, and wherein a camouflaging by the polymer of a charge site at the abnormal prion inactivates the transforming power.

* * * * *